United States Patent
Boykin et al.

(10) Patent No.: US 10,182,826 B2
(45) Date of Patent: Jan. 22, 2019

(54) SURGICAL CUTTING INSTRUMENT WITH NEAR-PERIMETER INTERLOCKING COUPLING ARRANGEMENT

(71) Applicant: Medtronic PS Medical, Inc., Fort Worth, TX (US)

(72) Inventors: Christopher M. Boykin, Athens, TX (US); Durrell Tidwell, Burleson, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 212 days.

(21) Appl. No.: 15/375,414

(22) Filed: Dec. 12, 2016

(65) Prior Publication Data

US 2017/0086856 A1 Mar. 30, 2017

Related U.S. Application Data

(63) Continuation of application No. 14/507,350, filed on Oct. 6, 2014, now Pat. No. 9,517,074, which is a continuation of application No. 12/136,935, filed on Jun. 11, 2008, now Pat. No. 8,852,221.

(51) Int. Cl.
*A61B 17/14* (2006.01)
*B27B 5/32* (2006.01)
(Continued)

(52) U.S. Cl.
CPC .......... *A61B 17/142* (2016.11); *A61B 17/14* (2013.01); *B27B 5/32* (2013.01); *B27B 19/006* (2013.01);
(Continued)

(58) Field of Classification Search
CPC ......... A61B 17/14; A61B 17/142; B27B 5/32; B27B 19/006
See application file for complete search history.

(56) References Cited

U.S. PATENT DOCUMENTS

| 81,661 A | 9/1868 | McDonald |
|---|---|---|
| 173,126 A | 2/1876 | Little |

(Continued)

FOREIGN PATENT DOCUMENTS

| AU | 2009257763 A1 | 12/2009 |
|---|---|---|
| CA | 2727401 A1 | 12/2009 |

(Continued)

OTHER PUBLICATIONS

Canadian Office Action dated Jul. 7, 2015 for Canadian Application No. 2727401 corresponding to PCT/US2009/045388 claiming benefit of U.S. Appl. No. 12/136,935, filed Jun. 11, 2008.

(Continued)

*Primary Examiner* — Christian Sevilla
(74) *Attorney, Agent, or Firm* — Harness Dickey

(57) ABSTRACT

A blade coupling mechanism for a hand-held surgical cutting instrument includes a first coupling member including a first blade-contacting surface and a first outer perimeter sidewall adjacent the first blade contacting surface. It also includes a second coupling member including a second blade-contacting surface facing the first blade-contacting surface of the first coupling member. The second coupling member includes a second outer perimeter sidewall adjacent the second blade contacting surface. The second blade-contacting surface and the second outer perimeter sidewall meet to define an outer edge. The second coupling member including a bore through the second blade contacting surface. The bore and the second blade contacting surface meeting to define an inner edge. Blade-engaging protrusions project from at least one of the first and second blade-contacting surfaces. The protrusions are spaced closer to the outer edge than the inner edge.

20 Claims, 11 Drawing Sheets

(51) Int. Cl.
*B27B 19/00* (2006.01)
*A61B 17/00* (2006.01)

(52) U.S. Cl.
CPC .......... *A61B 2017/00398* (2013.01); *A61B 2017/00473* (2013.01); *A61B 2017/00477* (2013.01); *A61B 2017/00526* (2013.01); *A61B 2017/00734* (2013.01); *Y10T 29/49899* (2015.01)

(56) References Cited

U.S. PATENT DOCUMENTS

| | | |
|---|---|---|
| 197,650 A | 11/1877 | Milligan |
| 336,661 A | 2/1886 | Peck |
| 519,892 A | 5/1894 | Newton |
| 3,554,197 A | 1/1971 | Dobbie |
| 3,656,393 A | 4/1972 | Goellner |
| 3,678,934 A | 7/1972 | Warfield et al. |
| 3,927,893 A | 12/1975 | Dillon et al. |
| 3,943,934 A * | 3/1976 | Bent ............... B27B 5/32 606/178 |
| 3,952,412 A | 4/1976 | Rhodes |
| 3,978,862 A | 9/1976 | Morrison |
| 4,106,181 A | 8/1978 | Mattchen |
| 4,386,609 A * | 6/1983 | Mongeon ............... B23D 51/10 30/339 |
| 4,513,742 A | 4/1985 | Arnegger |
| 4,584,999 A | 4/1986 | Arnegger |
| 4,617,930 A | 10/1986 | Saunders |
| 4,620,369 A | 11/1986 | Gercken |
| 4,637,391 A * | 1/1987 | Schlein ............... A61F 15/02 30/133 |
| 4,657,428 A | 4/1987 | Wiley |
| 4,739,557 A | 4/1988 | Wagner |
| 4,819,334 A | 4/1989 | Mongeon |
| 4,841,638 A | 6/1989 | Bardeen et al. |
| 5,002,555 A | 3/1991 | Petersen |
| 5,042,983 A | 8/1991 | Rayhack |
| 5,092,869 A | 3/1992 | Waldron |
| 5,122,142 A | 6/1992 | Pascaloff |
| 5,133,728 A | 7/1992 | Petersen |
| 5,135,533 A | 8/1992 | Petersen et al. |
| 5,178,626 A | 1/1993 | Pappas |
| D337,160 S | 7/1993 | Evans |
| 5,263,972 A | 11/1993 | Evans et al. |
| 5,265,343 A | 11/1993 | Pascaloff |
| D343,247 S | 1/1994 | Walen |
| D346,318 S | 4/1994 | Evans |
| 5,306,285 A | 4/1994 | Miller et al. |
| D348,194 S | 6/1994 | Tanis |
| 5,366,312 A | 11/1994 | Raines |
| D353,888 S | 12/1994 | Raines |
| 5,382,249 A * | 1/1995 | Fletcher ............... B23D 51/10 606/176 |
| 5,423,845 A | 6/1995 | McDaniel |
| D360,946 S | 8/1995 | Goris |
| D361,029 S | 8/1995 | Goris |
| 5,439,472 A | 8/1995 | Evans et al. |
| D362,065 S | 9/1995 | Goris |
| 5,468,247 A | 11/1995 | Matthai et al. |
| 5,489,285 A | 2/1996 | Goris |
| 5,496,316 A | 3/1996 | Goris |
| 5,507,763 A | 4/1996 | Petersen et al. |
| 5,544,511 A | 8/1996 | Cavaleri |
| 5,554,165 A | 9/1996 | Raitt et al. |
| 5,658,304 A | 8/1997 | Lim |
| 5,676,680 A | 10/1997 | Lim |
| 5,694,693 A | 12/1997 | Hutchins et al. |
| 5,697,158 A | 12/1997 | Klinzing et al. |
| 5,702,415 A | 12/1997 | Matthai et al. |
| 5,729,904 A | 3/1998 | Trott |
| 5,735,866 A * | 4/1998 | Adams ............... B23D 61/006 30/339 |
| D394,315 S | 5/1998 | Fisher |
| 5,839,196 A | 11/1998 | Trott |
| 5,846,244 A | 12/1998 | Cripe |
| D404,485 S | 1/1999 | Hutchins et al. |
| D405,177 S | 2/1999 | Hutchins et al. |
| D406,223 S | 3/1999 | Tran |
| 5,888,200 A | 3/1999 | Walen |
| RE36,269 E | 8/1999 | Wright |
| 5,941,891 A | 8/1999 | Walen |
| 6,007,541 A | 12/1999 | Scott |
| 6,022,353 A | 2/2000 | Fletcher et al. |
| 6,045,564 A | 4/2000 | Walen |
| 6,113,618 A | 9/2000 | Nic |
| 6,113,619 A | 9/2000 | Pascaloff |
| 6,126,670 A | 10/2000 | Walker et al. |
| 6,302,406 B1 | 10/2001 | Ventura |
| 6,332,836 B1 | 12/2001 | Tseng |
| D455,490 S | 4/2002 | Pascaloff |
| D459,805 S | 7/2002 | Pascaloff |
| 6,503,253 B1 | 1/2003 | Fletcher et al. |
| 6,656,186 B2 | 12/2003 | Meckel |
| 6,723,101 B2 | 4/2004 | Fletcher et al. |
| D489,823 S | 5/2004 | Fisher et al. |
| D492,412 S | 6/2004 | Desoutter et al. |
| 6,949,110 B2 | 9/2005 | Ark et al. |
| 7,001,403 B2 | 2/2006 | Hausmann et al. |
| 7,003,888 B2 | 2/2006 | Bigden et al. |
| 7,040,023 B2 | 5/2006 | Nemazi et al. |
| 7,147,550 B2 | 12/2006 | Chen |
| D536,791 S | 2/2007 | Eskridge et al. |
| 7,189,239 B2 | 3/2007 | Fisher et al. |
| 7,217,177 B2 | 5/2007 | Frech et al. |
| 7,833,241 B2 | 11/2010 | Gant |
| 8,523,868 B2 | 9/2013 | Boykin et al. |
| 8,640,580 B2 | 2/2014 | Bohne |
| 8,852,221 B2 | 10/2014 | Boykin et al. |
| 2002/0116023 A1 | 8/2002 | Fletcher et al. |
| 2002/0198556 A1 | 12/2002 | Ark et al. |
| 2003/0032971 A1 | 2/2003 | Hausmann et al. |
| 2003/0199880 A1 | 10/2003 | Meckel |
| 2004/0138668 A1* | 7/2004 | Fisher ............... B23D 51/10 606/82 |
| 2004/0199167 A1 | 10/2004 | Fletcher et al. |
| 2004/0204731 A1 | 10/2004 | Gant |
| 2004/0258497 A1 | 12/2004 | Krondorfer |
| 2006/0288837 A1 | 12/2006 | Utz et al. |
| 2007/0088330 A1 | 4/2007 | House |
| 2008/0119860 A1 | 5/2008 | McCarthy |
| 2009/0312779 A1 | 12/2009 | Boykin et al. |
| 2013/0204255 A1 | 8/2013 | Milburn et al. |
| 2014/0074098 A1 | 3/2014 | Boykin et al. |
| 2015/0025535 A1 | 1/2015 | Boykin et al. |

FOREIGN PATENT DOCUMENTS

| | | |
|---|---|---|
| CN | 102098971 A | 6/2011 |
| DE | 4036904 C1 | 5/1992 |
| EP | 0554929 A1 | 8/1993 |
| EP | 0776634 A2 | 6/1997 |
| EP | 0554929 B1 | 9/1999 |
| EP | 0776634 B1 | 9/2003 |
| EP | 2362749 A1 | 9/2011 |
| JP | H05253234 A | 5/1993 |
| JP | 2008505699 A | 2/2008 |
| JP | 2011-512624 A | 4/2011 |
| JP | 2011523884 A | 8/2011 |
| WO | WO-9513020 A1 | 5/1995 |
| WO | WO-9710765 A1 | 3/1997 |
| WO | WO-2006017066 A2 | 2/2006 |
| WO | WO-2007041027 A2 | 4/2007 |
| WO | WO-2009151959 A1 | 12/2009 |
| WO | WO-2009151965 A1 | 12/2009 |

OTHER PUBLICATIONS

China Fourth Office Action dated Sep. 30, 2013 for Chinese Application No. 200980128817.4 corresponding to PCT/2009/045388 claiming benefit of U.S. Appl. No. 12/136,935, filed Jun. 11, 2008.

(56) References Cited

OTHER PUBLICATIONS

China Third Office Action for Chinese Application No. 200980128817.4 dated May 6, 2013 corresponding to PCT/US2009/045388 claiming benefit of U.S. Appl. No. 12/136,935, filed Jun. 11, 2008.
Chinese First Office Action for Chinese Application No. 200980128817.4 dated Oct. 10, 2012 corresponding to PCT/US2009/045429 claiming benefit of U.S. Appl. No. 12/136,917 filed Jun. 11, 2008.
European Communication Pursuant to Article 94(3) EPC dated Apr. 15, 2014 for European Application No. 09763250.9 corresponding to PCT/US2009/045388 claiming benefit of U.S. Appl. No. 12/136,935, filed Jun. 11, 2008.
Extended Search Report dated Jun. 17, 2016 for European Application No. 16154725.2-1654 corresponding to PCT/US2009/045388 claiming benefit of U.S. Appl. No. 12/136,935, filed Jun. 11, 2008.
International Preliminary Report on Patentability dated Dec. 23, 2010 for PCT/US2009/45388 which claims benefit of U.S. Appl. No. 12/136,935, filed Jun. 11, 2008.
International Search Report and Written Opinion dated Oct. 28, 2009 for PCT/US2009/45388 which claims benefit of U.S. Appl. No. 12/136,935, filed Jun. 11, 2008.
Japanese First Office Action for Japanese Patent Application No. 2011-513549 dated Aug. 2, 2013 corresponding to PCT/US2009/045388 claiming benefit of U.S. Appl. No. 12/136,935, filed Jun. 11, 2008.
Japanese Second Office Action dated Apr. 11, 2014 for Japanese Patent Application No. 2011-513549 corresponding to PCT/US2009/045388 claiming benefit of U.S. Appl. No. 12/136,935, filed Jun. 11, 2008.
Indian Office Action dated Feb. 22, 2018 in corresponding Indian Application No. 4698/KOLNP/2010.

\* cited by examiner

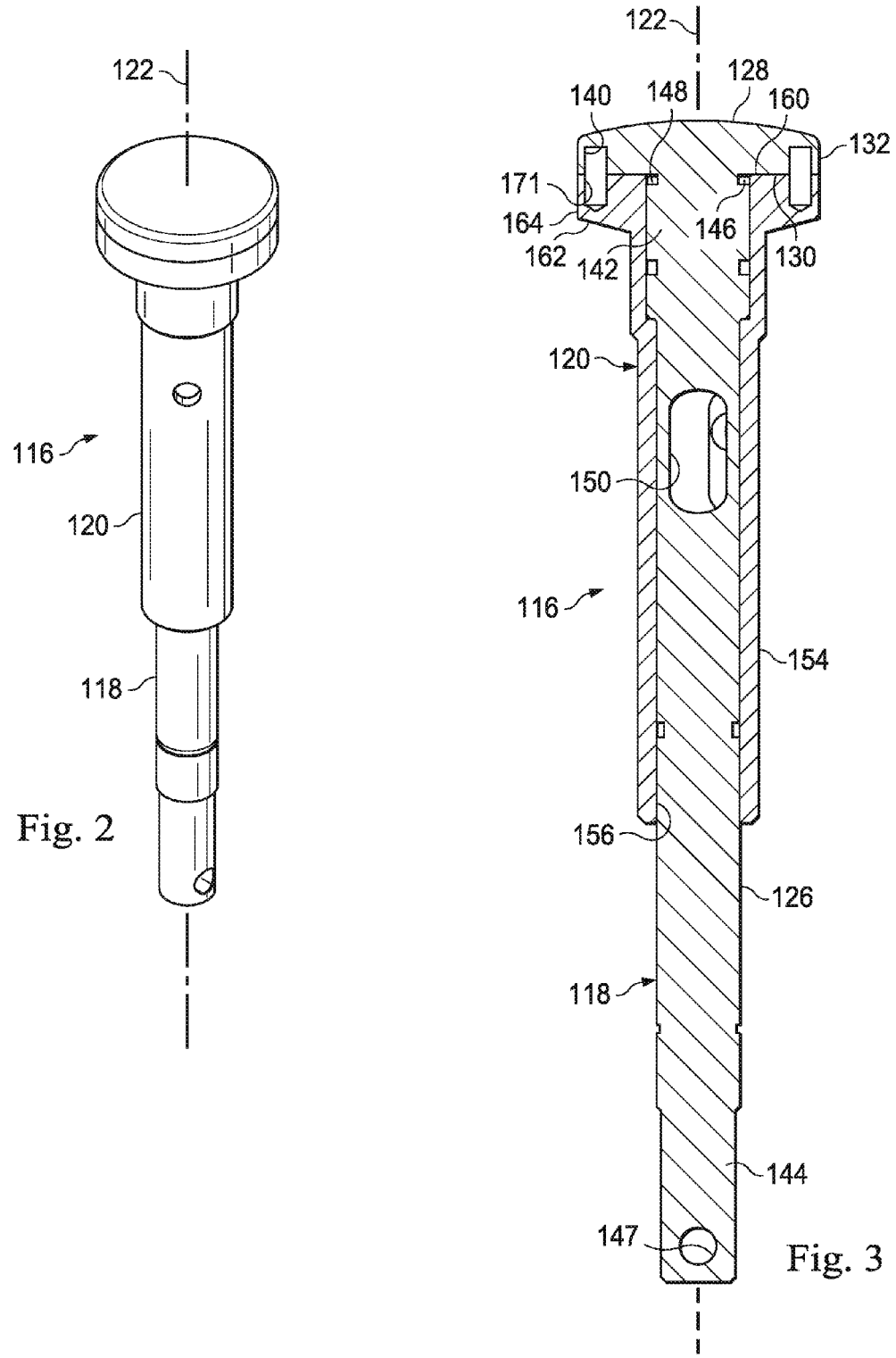

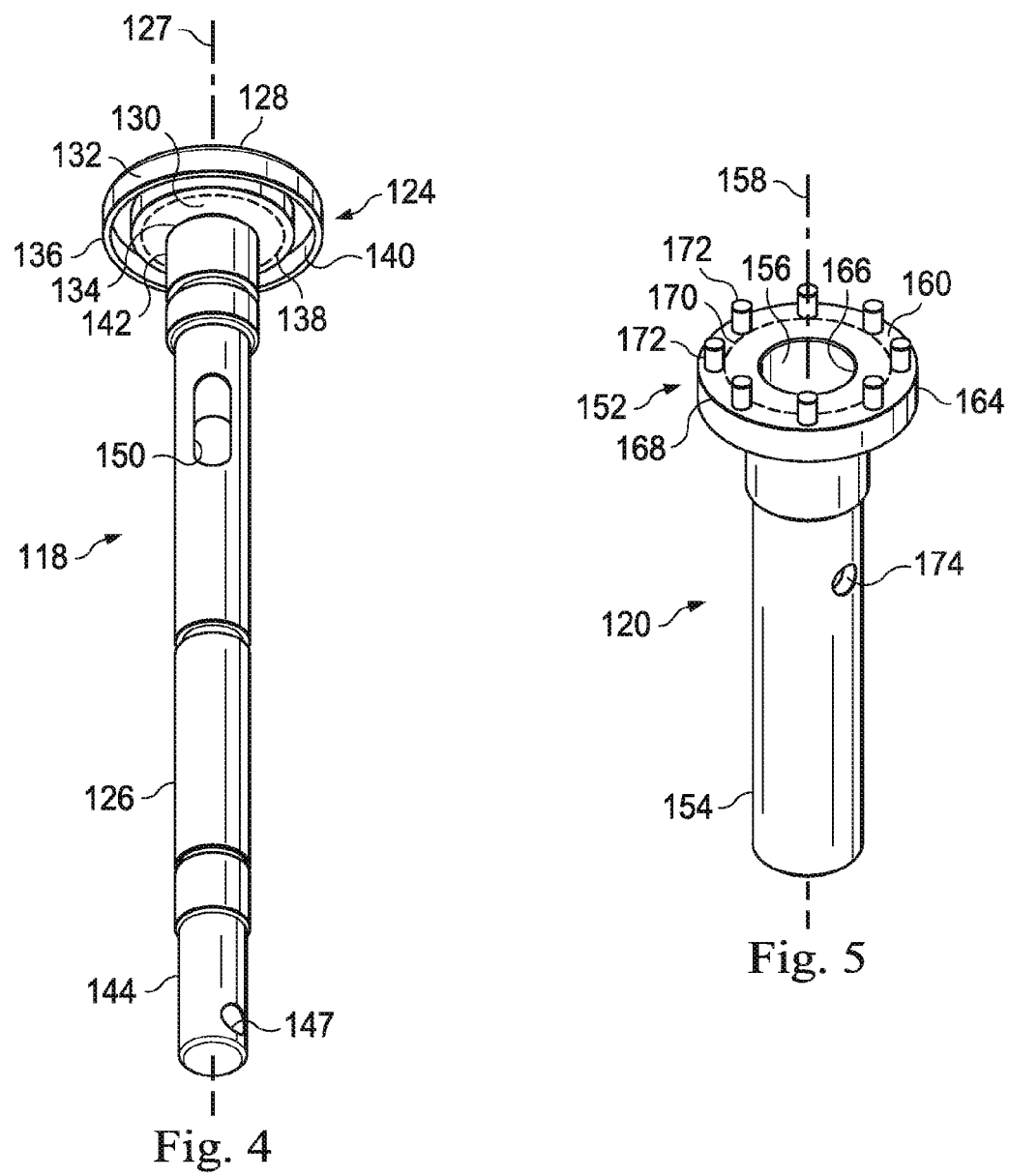

SURGICAL CUTTING INSTRUMENT WITH NEAR-PERIMETER INTERLOCKING COUPLING ARRANGEMENT

CROSS-REFERENCE TO RELATED APPLICATIONS

This application is a continuation of U.S. patent application Ser. No. 14/507,350 filed on Oct. 6, 2014, which is a continuation of U.S. patent application Ser. No. 12/136,935 filed on Jun. 11, 2008, now U.S. Pat. No. 8,852,221 issued on Oct. 7, 2014. The entire disclosure of the above application is incorporated herein by reference.

FIELD

The present disclosure relates to a surgical cutting instrument, and more particularly, to a surgical cutting instrument with near-perimeter interlocking coupling arrangement.

BACKGROUND

This section provides background information related to the present disclosure which is not necessarily prior art.

Bone-cutting surgical saws, such as sagittal or oscillating type surgical saws, cut most effectively at very high speeds, such as for example, 10000-40000 cycles per minute. These high speeds introduce high levels of vibration and can cause blade wander during a cut. Accordingly, blade cuts typically have a thickness considerably greater than the width of the actual blade. For example, a cutting blade having a 0.015 inch thickness may be unable to cut a groove having a width of less than 0.030 inch. In addition, because the saws operate at such high speeds, the excessive vibration can quickly fatigue a surgeon's hand or wrist. As fatigue sets in, maintaining the same preciseness and accuracy may become more difficult.

A contributing problem is the way the blade attaches to the saw. Conventional systems use pins located close to the centerline of the blade attachment portion, resulting in a short moment arm for driving the blade. Accordingly, during irregular cutting, such as a while making a curved cut or a cut not along the path of the normal oscillating path of the saw blade, the blade can become dislodged, possibly causing some blade loosening. This can result in cuts having a width considerably larger than the blade width.

The devices disclosed herein overcome one or more of short-comings in the prior art.

SUMMARY

This section provides a general summary of the disclosure, and is not a comprehensive disclosure of its full scope or all of its features.

In a first exemplary aspect, the present disclosure is directed to a hand-held surgical cutting instrument for cutting bone material with a bone-cutting surgical blade shaped to fit the surgical cutting instrument. The cutting instrument comprises a hand-graspable body for manipulating the cutting instrument and a blade coupling mechanism attached to the body and being configured to attach to the bone-cutting surgical blade. The blade coupling mechanism includes a first coupling member including a first blade-contacting surface and a first outer perimeter sidewall adjacent the first blade contacting surface. It also includes a second coupling member including a second blade-contacting surface facing the first blade-contacting surface of the first coupling member. The second coupling member includes a second outer perimeter sidewall adjacent the second blade contacting surface. The second blade-contacting surface and the second outer perimeter sidewall meet to define an outer edge. The second coupling member including a bore through the second blade contacting surface. The bore and the second blade contacting surface meeting to define an inner edge. Blade-engaging protrusions project from at least one of the first and second blade-contacting surfaces. The protrusions are spaced closer to the outer edge than the inner edge.

In another exemplary aspect, the present disclosure is directed to a surgical cutting instrument including a hand-graspable body for manipulating the cutting instrument and a blade coupling mechanism attached to the body and being configured to attach to the bone-cutting surgical blade. The blade coupling mechanism includes a driving shaft having a shank defining an axis and a head. The head includes an outer surface, a first blade-contacting surface opposite the outer surface, and a first outer perimeter sidewall extending between the outer and first blade-contacting surfaces. The first blade-contacting surface and the first outer perimeter sidewall meet to define an outer edge. The first blade contacting surface and the shank meet to define an inner edge. The blade coupling mechanism also includes a sleeve having a bore formed therein, with the shank of the driving shaft being disposed in the bore. The sleeve has a second blade-contacting surface facing the first blade-contacting surface and has a second outer perimeter sidewall. A portion of the second outer perimeter sidewall is substantially aligned with a portion of the first outer perimeter sidewall of the driving shaft. The second blade-contacting surface and the second outer perimeter sidewall meet to define an outer edge. The bore and the second blade contacting surface meet to define an inner edge. The blade coupling mechanism also includes blade engaging protrusions extending from one of the first and second blade-contacting surfaces and includes at least one receiving recess formed in the other of the first and second blade-contacting surfaces. The blade engaging protrusions and the receiving recess are formed closer to the outer edges than the inner edges.

In yet another exemplary aspect, the present disclosure is directed to a surgical cutting instrument including a hand-graspable body for manipulating the cutting instrument and a blade coupling mechanism attached to the body and being configured to attach to the bone-cutting surgical blade. The blade coupling mechanism includes a first coupling member including a first blade-contacting surface and a first outer perimeter sidewall adjacent the first blade contacting surface. The first outer perimeter sidewall defines a central axis normal to the first blade contacting surface. The blade coupling mechanism also includes a second coupling member including a second blade-contacting surface facing the first blade-contacting surface of the first coupling member. The second coupling member includes a second outer perimeter sidewall adjacent the second blade contacting surface. A portion of the second outer perimeter sidewall is substantially aligned with a portion of the first outer perimeter sidewall. Blade-engaging protrusions project from at least one of the first and second blade-contacting surfaces. The protrusions have an outermost portion disposed closest to the first outer perimeter sidewall. The outermost portion is spaced from the central axis at least 80% of the distance from the axis to the first outer perimeter sidewall.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is an illustration of an exemplary collet assembly from the surgical system of FIG. 1.

FIG. 3 is an illustration of a cross-section of the exemplary collet assembly of FIG. 2.

FIG. 4 is an illustration of an exemplary driving shaft of the collet assembly of FIG. 2.

FIG. 5 is an illustration of an exemplary sleeve of the collet assembly of FIG. 2.

Corresponding reference numerals indicate corresponding parts throughout the several views of the drawings.

DETAILED DESCRIPTION

Figure 1:
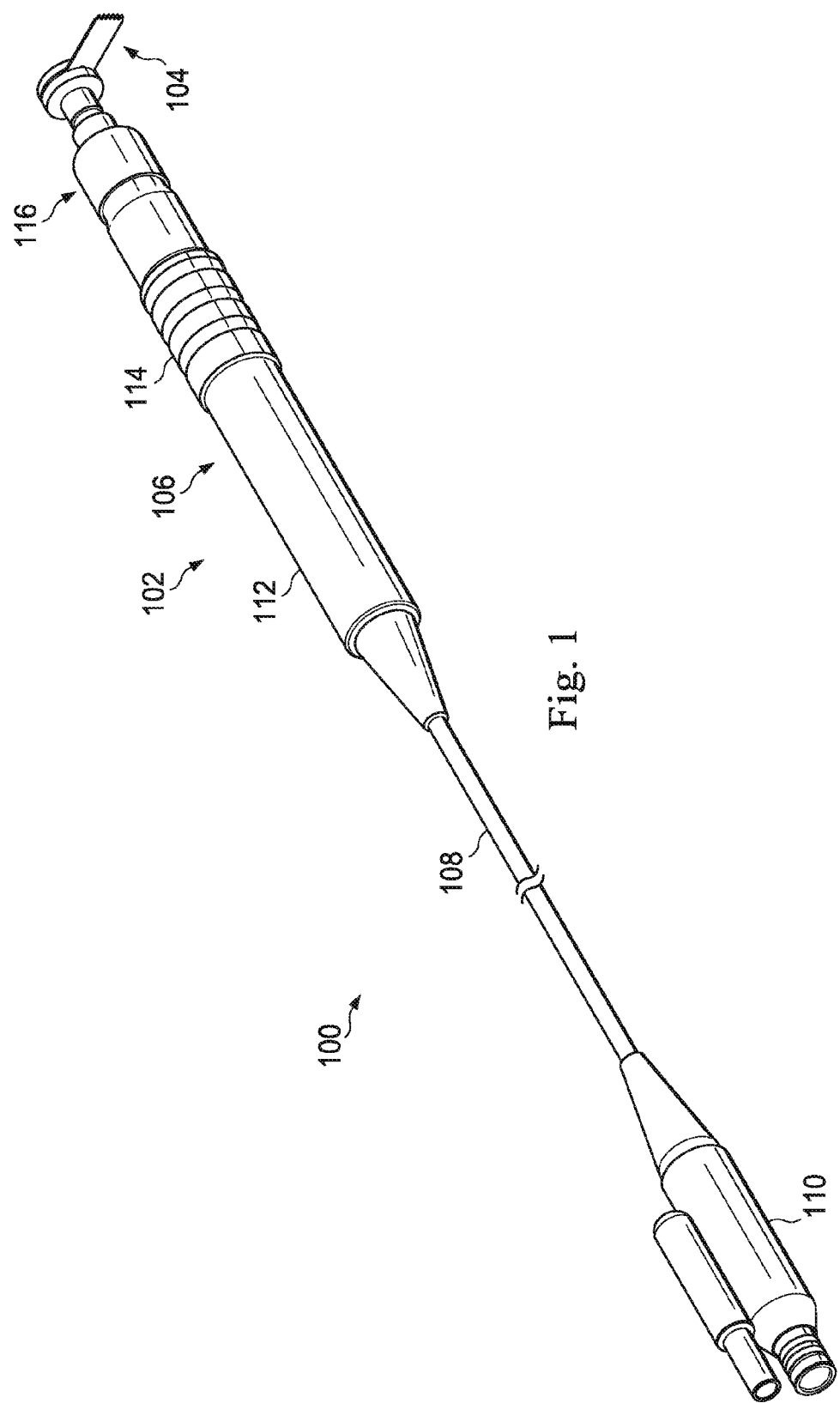
FIG. 1 is an illustration of an exemplary oscillating bone-cutting surgical system.

Example embodiments will now be described more fully with reference to the accompanying drawings.

For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Generally, the present disclosure relates to a bone cutting surgical system including a hand-held, high-speed, bone-cutting surgical saw, such as a sagittal or oscillating saw, and a cutting micro-saw blade. The saw includes a collet assembly with protruding pins or nubs that mesh with or extend into openings on the cutting blade, thereby securing the blade in place in the collet assembly. In order to minimize the moment forces on the interior of the blade when the blade is rotating, the protrusions on the collet assembly and the openings on the saw blade are placed toward the exterior perimeter of the collet assembly and the exterior perimeter of the saw blade. In one embodiment, the openings are notches formed along the exterior edge of the saw blade. By moving moment forces toward the exterior of the saw blade, blade vibration may be reduced. Reducing vibration increases cutting accuracy, which can reduce patient trauma and speed recovery time, as well as reduce surgeon fatigue. In some embodiments, the micro-saw blades include a dampening overmold that interfaces with the collet assembly. This too may reduce blade vibration. In addition, the overmold may assist with blade identification.

Turning now to FIG. 1, the present disclosure is directed to a bone-cutting surgical system 100 including a surgical saw 102 and a selectively removable micro-saw blade 104. The surgical saw 102 includes a hand-piece 106, a cord 108, and a connector 110 configured to removably couple with a power source. The connector 110 is merely exemplary, and it should be apparent to one skilled in the art that any suitable connector may be used, and in some embodiments, the cord 108 itself may be coupled to the power source without the use of a connector. Additional contemplated embodiments include a power source as a part of the hand-piece 106, such as a battery powered hand-piece.

The hand-piece 106 includes a motor assembly 112, a grip 114, and a collet assembly 116. In some embodiments, the motor assembly 112 is housed within the grip 114, while in other embodiments, it is disposed adjacent to the grip 114. It is contemplated that any suitable system for controlling the surgical saw 102 may be used. For example, some embodiments include a trigger system disposed on the hand-piece 106 to provide hand-control of the cutting speed, or alternatively, a foot pedal associated with the hand-piece 106 through the power source to provide the controlling inputs. Other control systems also are contemplated.

FIGS. 2-5 show a portion of the exemplary collet assembly 116. The collet assembly 116 secures the saw blade 104 to the surgical saw 104 and transfers a driving force from the motor to the blade. In this embodiment, it includes a driving shaft 118 and a sleeve 120 defining a longitudinal collet axis 122. The sleeve 120 receives and extends about the driving shaft 118 and is axially movable along the collet axis 122 relative to the driving shaft 118, enabling selective coupling with the blade 104.

The driving shaft 118 is shown in greater detail in FIGS. 3 and 4. Here, the driving shaft includes a head 124 forming a distal end of the driving shaft and a shank 126 extending proximally from the head 124. These together define a shaft axis 127 (FIG. 4) extending longitudinally through the shaft.

Referring to FIGS. 3 and 4, the head 124 includes a distally facing outer surface 128, a proximally facing blade contacting surface 130 adjacent the shank 126, and an outer perimeter 132 extending therebetween. The blade contacting surface 130 includes an inner edge 134, which in this embodiment is defined where the shank 126 and the blade contacting surface 130 meet. It also includes an outer edge 136, which in this embodiment is defined where the outer perimeter 132 and the blade contacting surface 130 meet. These inner and outer edges 134, 136 define a reference mid-line 138 half-way between them on the blade contacting surface 130.

In this embodiment, the blade contacting surface 130 includes a receiving opening formed therein as a receiving recess 140 for receiving one or more protrusions to be discussed below relative to the sleeve 120. Here, the receiving recess 140 is formed as a single groove concentric about the shaft axis 127 and disposed closer to the outer perimeter 132 than to the shank 126. Accordingly, as shown in FIG. 4, the receiving recess 140 is offset from the mid-line 138 defined by the inner and outer edges 134, 136 of the blade contacting surface 130. In the example shown, the outermost edge of the receiving recess 140 (edge closest to the outer perimeter 132) is located toward the outer edge 136 at least half of the distance between the mid-line 138 and the outer edge 136. Said another way, the outermost edge of the receiving recess 140 is located toward the outer edge 136 at least three quarters or 75% of the distance from the inner edge 134 to the outer edge 136. In some embodiments, the outermost edge of the receiving recess is closer to 80% of the distance between the inner edge 134 and the outer edge 136. In the embodiment shown, the inner most edge of the receiving recess 140 (edge closest to the shank 126) is likewise located more than half the distance toward the outermost edge 136 so that the entire receiving recess 140 is disposed outwardly from the midline 138, or more than half of the distance of the inner edge 134 to the outer edge 136.

Furthermore, in the example of FIG. 4, the outermost edge of the receiving recess 140 is disposed toward the outer edge 136 more than 80% of the distance from the shaft axis 127 to the outer edge 136, and in some embodiments, more than 90% of the distance from the shaft axis 127 to the outer edge 136.

The shank 126 includes a distal end 142 either connected to or integral with the head 124 and a proximal end 144. At the distal end 142, the shank includes a blade receiving radial groove or recess 146 (FIG. 3). The groove 146 is formed such that the blade contacting surface 130 of the head 124 forms one side of the groove 146 while the opposing side is formed by a shoulder portion 148 (FIG. 3) of the shank 126. In the embodiment shown, the groove 146 is formed with a circular diameter sized to mate with and receive a portion of the saw blade 104. However, in other embodiments, the groove 146 is non-circular, and may be formed, for example, of a series of flat surfaces or may be formed of, for example, two grooves formed into opposing sides of the shank 126. An axially elongated slot 150 extends through the shank 126. This can receive a pin (not shown) connecting the shank 126 to the sleeve 120 while still permitting limited axial sliding between the sleeve 120 and shank 126. In this embodiment, the proximal end 144 includes a motor coupling feature 147 shown as a pin-receiving through passage that connects either directly or cooperatively to the motor to provide the cutting oscillation required.

FIGS. 3 and 5 show the sleeve 120 in greater detail. The sleeve 120, like the driving shaft 118, includes a head 152 and a shank 154, but is formed with a central bore 156 sized to receive the shank 126 of the driving shaft 118 as shown best in FIG. 3. The sleeve 120 defines a sleeve axis 158 shown in FIG. 5. The head 152 includes a substantially planar distally facing blade contacting surface 160, a proximally facing surface 162, and an outer perimeter 164. In this embodiment, the sleeve outer perimeter 164 is sized to have substantially the same diameter as the driving shaft outer perimeter 132. Further, as shown in FIG. 3, the distally facing blade contacting surface 160 of the sleeve 120 faces the proximally facing blade contacting surface 130 of the driving shaft 118.

The distally facing blade contacting surface 160 includes an inner edge 166, which in this embodiment is defined where the central bore 156 and the distally facing blade contacting surface 160 meet. It also includes an outer edge 168, which in this embodiment is defined where the outer perimeter 164 and the distally facing blade contacting surface 160 meet. These inner and outer edges 166, 168 define a reference midline 170 extending half-way between them on the distally facing blade contacting surface 160.

Referring now to FIG. 5, the distally facing blade contacting surface 160 of the sleeve 120 includes a plurality of protrusions 172 formed thereon. These are symmetrically disposed about the sleeve axis 158 and are configured to interface with the saw blade 104, as is further discussed below. Here, the sleeve 120 includes eight protrusions extending therefrom, spaced apart about the sleeve axis 158. It is contemplated that more or fewer protrusions may be present. The protrusions 172 may be integrally formed with sleeve 120 or, for manufacturing convenience, may be separate components fit, such as with an interference fit, into receiving ports 171 (shown in FIG. 3) formed in the distally facing blade contacting surface 160. For clarity, the protrusions 172 are not shown in FIG. 3, but are shown in FIG. 5. In this embodiment, these protrusions 172 are formed of cylindrical pins extending from the substantially planar distally facing blade contacting surface 160. In other examples however, the protrusions 172 have a square, rectangular, triangular or diamond-shaped cross-section. Protrusions of other shapes are also contemplated.

The protrusions 172 are disposed offset from the mid-line 170 on the distally facing blade contacting surface 160. In the example shown, the protrusions 172 are disposed so that the outermost portion of the protrusions (portion of protrusion closest to the perimeter 164) is located toward the outer edge 1688 at least half of the distance between the midline 138 and the outer edge 168. Said another way, the outermost portions of the protrusions 172 are located toward the outer edge 168 at least three quarters or 75% of the distance from the inner edge 166 to the outer edge 168. In some embodiments, the outermost portions of the protrusions 172 are closer to 80% of the distance between the mid-line 170 and the outer edge 168.

In the embodiment shown, the inner most portions of the protrusions 172 (portions closest to the inner edge 166) are likewise located toward the outermost edge 136 so that the entire protrusion 172 is disposed outwardly from the midline 170, or more than half of the distance of the inner edge 166 to the outer edge 168.

Furthermore, in the example of FIG. 5, the outermost portions of the protrusions are disposed toward the outer edge 168 more than 80% of the distance from the sleeve axis 158 to the outer edge 168, and in some embodiments, more than 90% of the distance from the sleeve axis to the outer edge 168.

The sleeve shank 154 extends from the proximally facing surface 162 (FIG. 3) of the head 152 and includes a transverse through hole 174 in each side sized to receive a pin (not shown) connecting the sleeve 120 and driving shaft 118. When assembled with the driving shaft 118, the hole 174 aligns with the slot 150 in the driving shaft 118 for slidable, pinned attachment.

Referring now to FIG. 3, as can be seen, the distally facing blade contacting surface 160 of the sleeve 120 and the blade contacting surface 130 of the driving shaft 118 face each other. The pieces may axially move apart to receive the blade 104, and then come together to clamp the blade 104 between the blade contacting surfaces. When assembled, the shaft axis 127 (FIG. 4) of the driving shaft 118 and the sleeve axis 158 (FIG. 5) of the sleeve are co-axially aligned with the longitudinal collet axis 122 (FIG. 3). These form a centerline about which the saw blade 104 can oscillate. The protrusions 172 (not shown for clarity in FIG. 3) extending from the distally facing blade contacting surface 160 fit within the receiving recess 140 formed in the head of the driving shaft 118 to both secure and align the saw blade 104, as discussed below.

Here, the receiving recess 140 is shown as a single groove formed radially about the shaft axis 127, and extending into the proximally facing blade contacting surface 130. In some embodiments, the collet assembly 116 includes no receiving recess, but the protrusions extend to and abut directly against the substantially planar proximally facing blade contacting surface 130.

Figure 6:
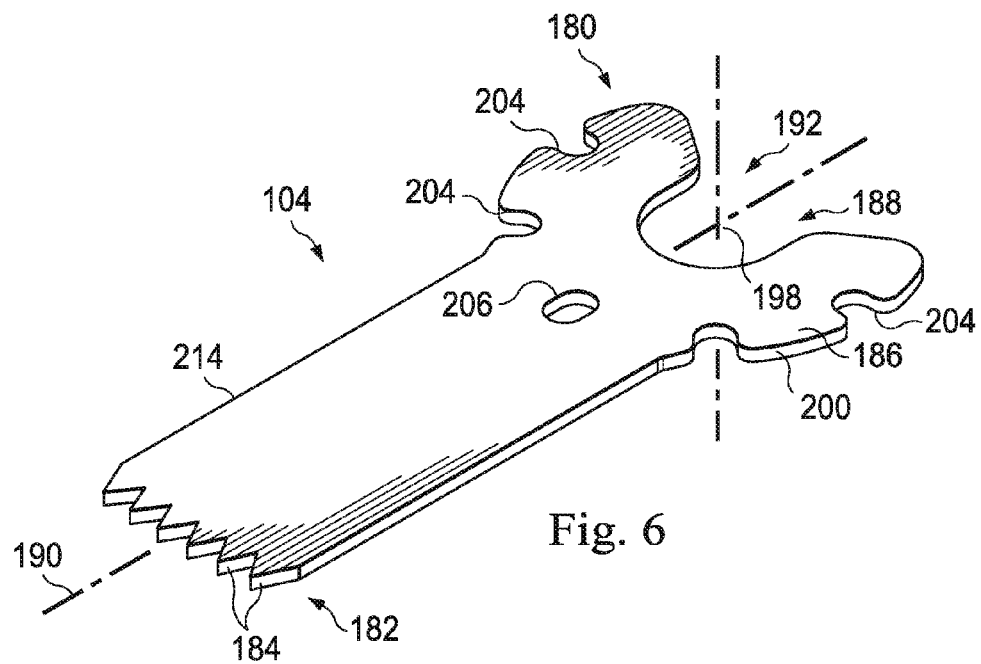
FIGS. 6 and 7 are illustrations of an exemplary micro-saw blade of the bone cutting surgical system of FIG. 1.
Figure 7:
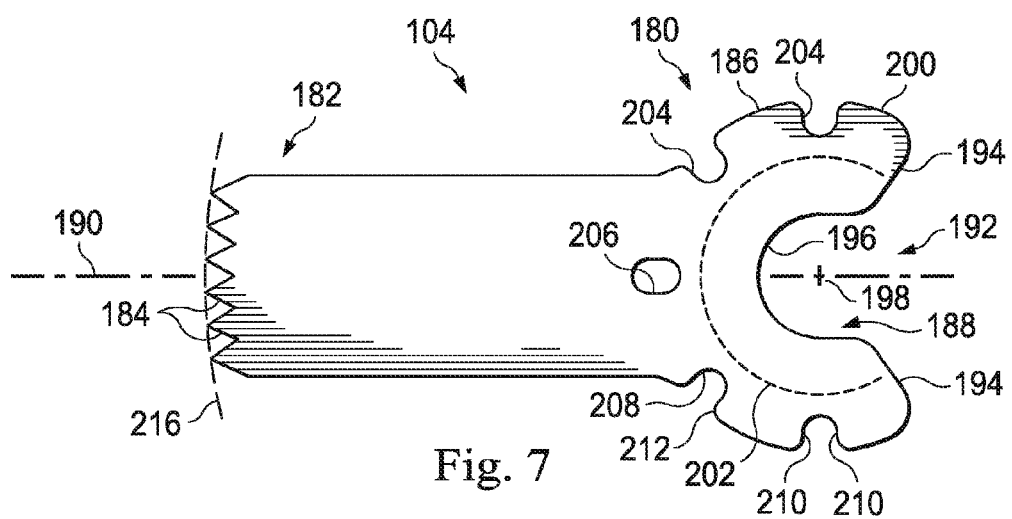

FIGS. 6 and 7 show the exemplary micro-saw blade 104 usable with the surgical saw 102 in FIG. 1 and securable with the collet assembly 116 in FIGS. 2-5. The micro-saw blade 104 includes a proximal end 180 that that facilitates interconnection with the collet assembly 116 and a distal end 182 having a cutting edge including a plurality of cutting teeth 184 formed thereon.

In this example, the proximal end 180 is defined by a relatively bulbous head 186 that includes a slot 188 extending inwardly along a longitudinal axis 190 form the proximal end of the saw blade 104. The slot 188 is formed with a funnel-like opening 192 defined by substantially straight edges 194 facing toward the longitudinal axis 190. The straight edges may help guide the saw blade 104 into place on the collet assembly, and form an angle between 70 and 160 degrees, but more particularly, within a range of about 90 to 120 degrees. The slot 188 also includes a slot edge 196 shaped to interface with the blade receiving groove 146 on the driving shaft 118 (FIG. 3). Because the blade receiving groove 146 is cylindrically shaped, the slot edge 196 is formed as a semi-circle, about a center point 198 defined by the bulbous head 186, with substantially parallel sides extending proximally from the slot edge toward the funnel-like opening 192. The slot edge 196 at least in part defines an inner edge of the bulbous head 186. A partially circular outer perimeter 200, which in this embodiment is concentric with the slot edge 196, defines an outer edge of the bulbous head 188. In some embodiments, the outer perimeter 200 has a diameter substantially the same as, or slightly smaller than, the diameter of the driving shaft head 124 and the sleeve head 152. For reference, a concentric midline 202 splits the distance between the outer perimeter 200 and the slot edge 196 in FIG. 7.

Openings 204 formed in the outer perimeter 200 and extending through the blade 104 permit the saw blade 104 to be secured to the surgical saw collet assembly 116. In the embodiment shown, the openings 204 are symmetrically disposed about the center point 198. Here, at least two openings 204 lie directly on opposing sides of the center point and on transverse sides of the longitudinal axis 190. A centrally disposed opening 206 lies along the longitudinal axis 190. The central opening 206 is spaced the same distance from the center point 198 as the perimeter openings 204. In the example shown the openings 204, 206 are offset from each other by 45 degrees and are sized to match the protrusions 172 on the distally facing surface of the sleeve 120. However, other offset angles are contemplated that match the desired collet assembly.

The openings 204, 206 are disposed offset from the mid-line 202 defined by the outer perimeter 200 and the slot edge 196 of the bulbous head 186. In the example shown, the openings 204, 206 are formed so that innermost edge portions (edge portions closest to the centerpoint 198) are disposed closer to the outer perimeter 200 than to the slot edge 196. Accordingly, the innermost edge of the opening is spaced from the slot edge 196 more than half of the distance between the outer perimeter 200 and the slot edge 196. In some embodiments, the innermost edge portions of the openings 204, 206 are spaced toward the perimeter edge to be more than about 70% of the distance between the outer perimeter 200 and the slot edge.

Furthermore, as measured from the centerpoint 198, the innermost edge portions of the openings may be located toward the outer perimeter 200 more than 80% of the distance between the perimeter 200 and the centerpoint 198, and in other embodiments, more than 90% of the distance between the perimeter 200 and the centerpoint 198.

Each opening 204, 206 is shaped to be slot-like, having a semi-circular inner end 208 and substantially parallel sides 210, albeit for a relatively short distance, extending from the semi-circular end 208 toward the outer perimeter 200. Chamfered or rounded edges 212 smooth the transition from the opening 204 to the outer perimeter 200. This reduces the chance of snagging or perforating surgical gloves on the proximal end 180 of the saw blade 104. This is particularly useful because the outer perimeter 200 may be closely aligned with, or slightly smaller than the outer perimeters of the heads of the driving shaft and sleeve. It is noted that the transition from the outer perimeter 200 to the straight edges 194 of the slot opening 192 are also chamfered or rounded.

In the example shown, the bulbous head 186 includes five openings 204, 206. However, in other embodiments, more or less openings may be provided. When the funnel-like opening 192 has an angle smaller than that shown, additional openings may be included, while maintaining the 45 degree spacing shown.

The saw blade 104 includes a shank 214 interposed between the proximal end 180 and the distal end 182. The distal end 182 of the saw blade 104 includes the plurality of teeth 184 formed at angles of 60 degrees, however, other angles, both larger and smaller are contemplated. The cutting teeth angle may be at least partially dependent on the surgical application. In the embodiment shown, tips of the teeth are formed so that together, the teeth define a circular path, indicated by the reference line 216.

Figure 8:
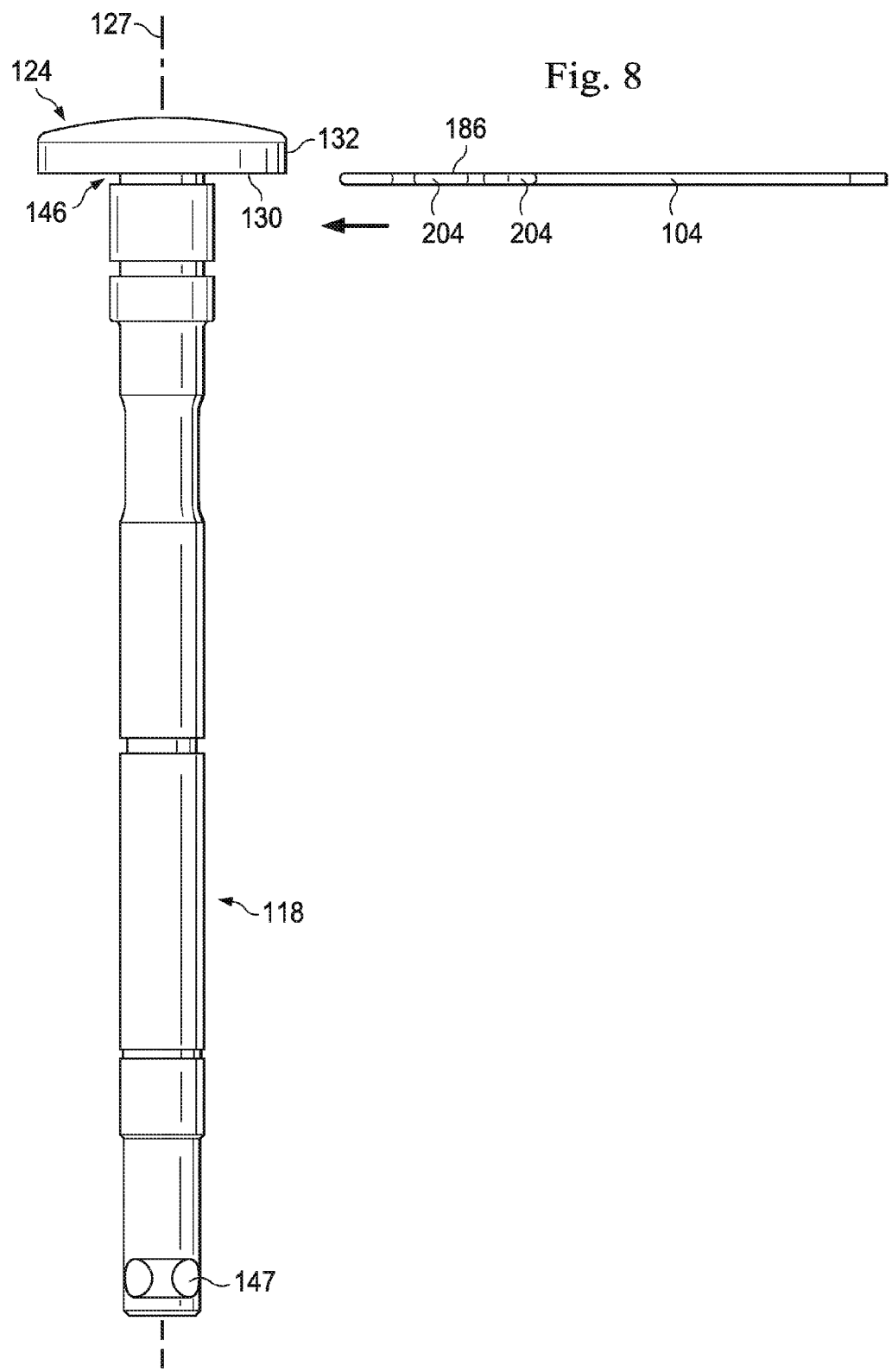
FIG. 8 is an illustration of the driving shaft of FIG. 3 with a micro-saw blade.
Figure 9:
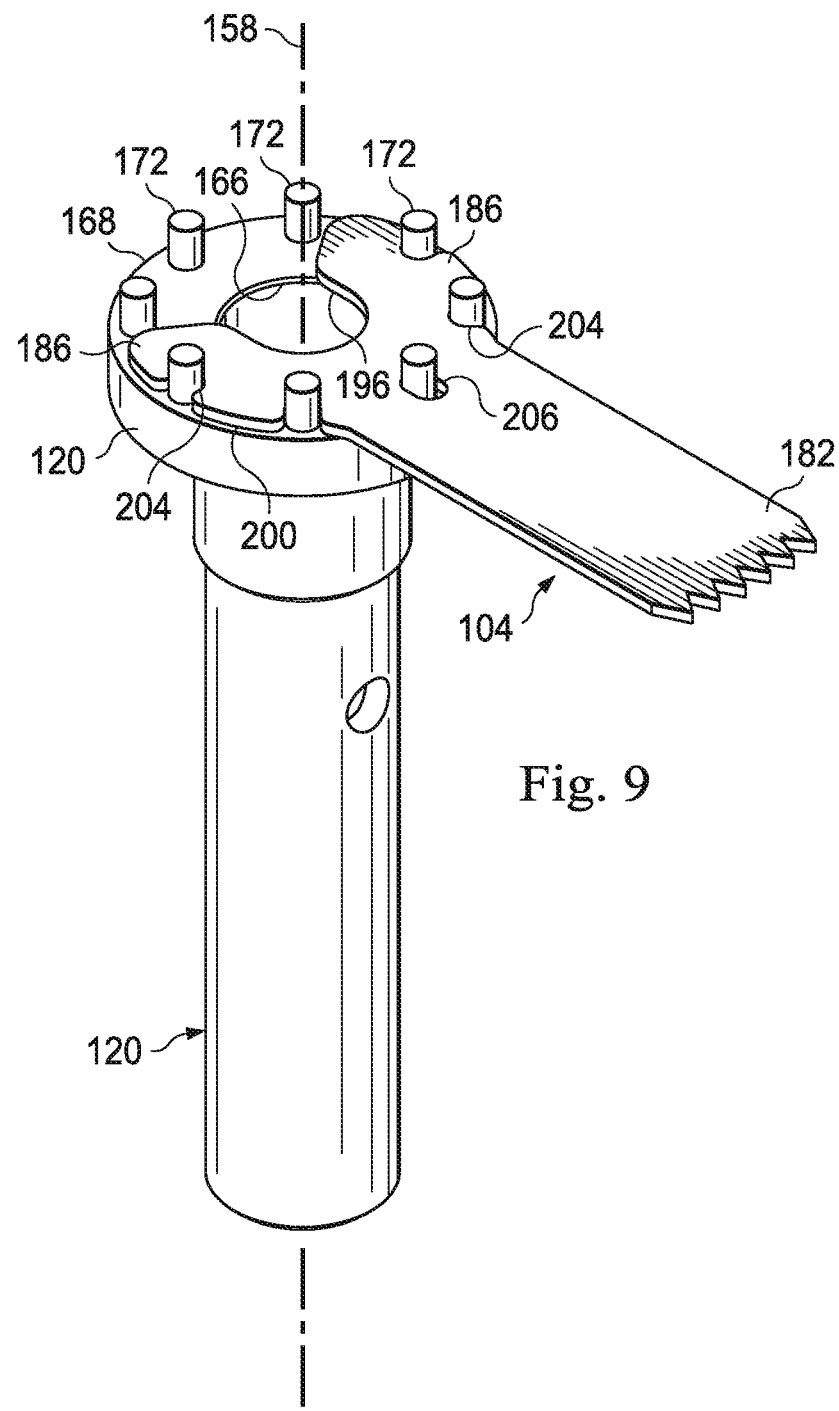
FIG. 9 is an illustration of the sleeve of FIG. 4 with an in-place micro-saw blade.

FIGS. 8 and 9 respectively show the blade 104 with reference to the driving shaft 118 and the sleeve 104, respectively. Although the blade 104 is shown separately with respect to each of the shaft and sleeve, when the driving shaft 118 and the sleeve 104 are joined together to form the collet assembly 116, it is contemplated that a single blade will be used at a time, although other arrangements are possible. First, with reference to FIG. 8, the bulbous head 186 of the blade 104 fits partially within the blade receiving groove 146. In order to provide a secure fit, the slot 188 (FIG. 7) is formed with a diameter that easily receives the inner portion of the receiving groove 146, but also has a clearance close enough to provide some stabilizing support to the blade 104. The bulbous head 186 of the saw blade 104 is substantially the same size or slightly smaller than as the outer perimeter of the head of the driving shaft. It should be noted that when the blade 104 is properly received in the receiving groove 146, the center point 198 of the blade 104 is aligned with the shaft axis 127, such that the outer perimeter 200 of the blade 104 and the outer perimeter 132 of the shaft head 124 are concentric. During assembly, the blade 104 is first introduced into the receiving groove 146 adjacent the blade contacting surface 130 of the shaft head 124 so that the bulbous head 186 lies flush with the blade contacting surface 130, as indicated by the arrow. The sleeve 120 is then axially slid along the shaft 118 so that the protrusions 172 (not shown in FIG. 8) engage the openings 104, 106 in the blade 104.

FIG. 9 shows the protrusions 172 of the sleeve 120 interfacing with the openings 204, 206 on the bulbous head 186 of the micro-saw blade 104, without the driving shaft 118. In some embodiments, when assembled with the driving shaft 118, the protrusions 172 extend through the openings 204, 206 and extend at least partially into the receiving recess 140 on the driving shaft 116 (FIG. 3). In other embodiments, the protrusions 172 have a length substantially the same as the thickness of the bulbous blade head 186 such that the protrusions just abut against or lie substantially flush with the proximally facing blade contacting surface 130 of the driving shaft 118 (FIG. 4).

In the example shown, the saw blade 104 has only five openings and receives five protrusions 172. In other embodiments, the saw blade 104 has more or fewer openings that receive the protrusions. In one example, the blade 104 includes seven openings and receives seven protrusions. Because the protrusions are spaced 45 degrees apart, the blade 104 can be removed and secured onto the sleeve in eight different positions. In some embodiments, for example, the sleeve includes only four protrusions or six protrusions, and the openings on the blade 104 are chosen to correspond with the protrusions.

It should be noted that when the blade 104 is properly disposed on the sleeve 120, the center point 198 of the blade 104 aligns with the sleeve axis 158, such that the outer perimeter 200 of the blade 104 and the outer perimeter 164 of the head of the sleeve 120 are concentric.

Because the sleeve protrusions 172 are disposed closer to the outer edge 168 than the inner edge 166, and likewise, because the blade openings 204 are disposed closer to the perimeter 200 than the slot edge 196, the protrusions 172 provide a longer moment arm than conventional systems, thereby providing higher torque with the same forces. This in turn increases the torque at the distal end 182 of the saw blade 104, permitting an equivalent torque while reducing the motor force, or alternatively, using the same motor force to provide increased cutting force. In addition, by increasing the distance of the moment arm from the blade centerpoint to the protrusions, there is less moment placed on the interior portions of the blade when it is oscillating. This may reduce vibration that might otherwise occur, in turn potentially reducing the amount of play and increasing accuracy achievable with the cutting blade 104. By providing openings 204, 206 on the blade 104 relatively far from the centerpoint of the shaft, the moment force at the distal end 182 of the blade 104 may be maximized.

Figure 10:
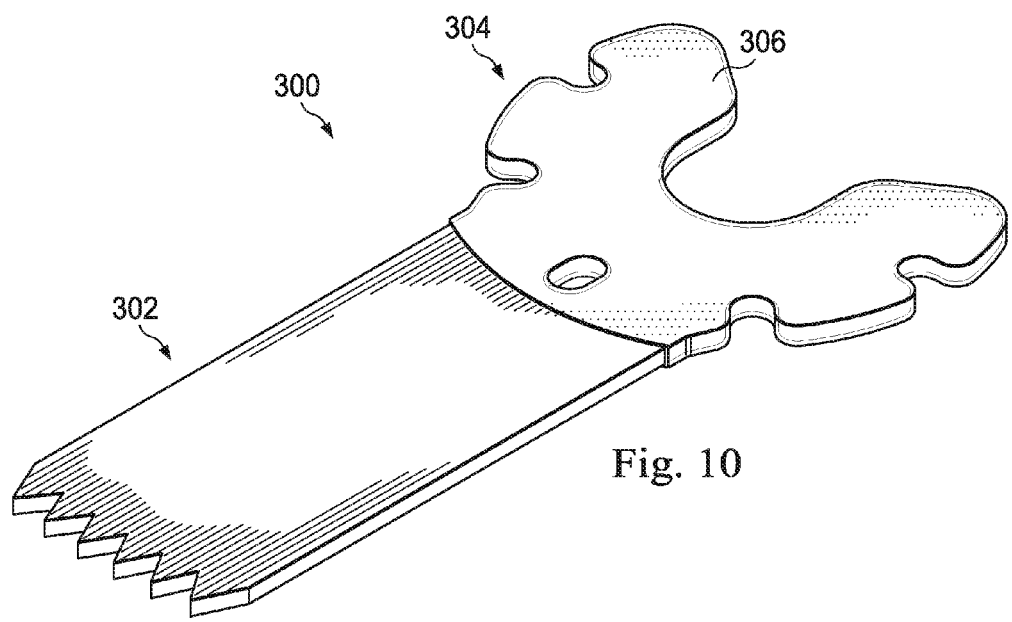
FIGS. 10-12 are illustrations of additional exemplary micro-saw blades usable with the bone-cutting surgical system.

FIG. 10 shows an alternative embodiment of a micro-saw blade, referenced by the reference numeral 300. Many of the features of the micro-saw blade 300 are similar to those of the micro-saw blade 104 discussed previously. Accordingly, only the differences are addressed in detail here. Here, the saw blade 300 is formed of a first material such as a single stamped material that provides the distal cutting end 302, and also formed of a second material different than the first material that forms at least a part of the proximal end 304. In this example, in addition to forming the distal end 302, the first material forms a part of a bulbous head section 306. The second material is overmolded about the first material to also form a part of the bulbous head section 306. In some examples the second material at the bulbous head section 306 is formed of a material more compliant than the blade material. In some examples, the overmold is a polymer material molded over a cutting blade portion formed of a surgical steel. Some examples of materials for the overmold include, for example, biocompatible low density polyethylene or polypropylene. Other examples are formed of elastomers, including blends to achieve a desired strength or durability. However, any biocompatible material may be used.

As shown in FIG. 10, the overmold material is formed to have substantially the same profile as the cutting blade so that the protrusions on the collet assembly will securely attach the cutting blade 300 in the same manner as the cutting blade 104. Furthermore, during use, the overmold material provides some dampening and cushioning to the saw blade 300. This dampening may reduce vibration experienced by the surgeon, providing some relief to hand and arm fatigue, and also decreasing blade wobble, increasing accuracy of the cut. The overmold also provides additional protection to the surgeons fingers and surgical gloves, as the overmold may provide additional protection from sharp or rigid edges that may be located about the proximal end 304 of the saw blade 300.

Figure 11:
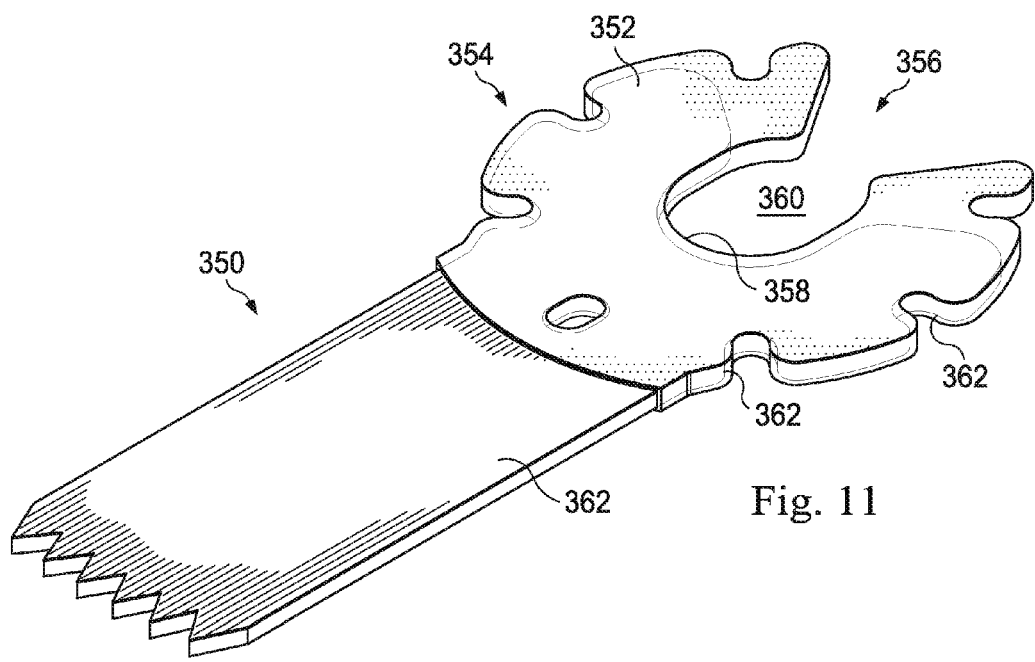

In the embodiment shown, the saw blade 300 may be secured to the sleeve 120 discussed above by five protrusions 172 out of eight since the most proximal portion of the bulbous head 306 forms the tapering opening. However, in an alternative embodiment, shown in FIG. 11, a saw blade referenced herein as 350 includes an overmold 352 forming a part of the bulbous head 354 that extends further around a slot opening 356, thereby at least partially enclosing an inner end 358 of the slot 360 in the saw blade 350. The slot 360 in the center of bulbous head 354 still receives the shank of the driving shaft 118. As shown in FIG. 11, while a blade portion 362 of the saw blade 350 appears to have a size substantially as discussed above, the overmold 352 itself extends about further, partially enclosing the slot 360. This overmold 352 deforms when the saw blade 350 is attached or detached from the collet assembly 116 to permit the shank 126 of the driving shaft 118 to enter the slot 360. In another embodiment, the overmold 352 completely encloses the slot 360 to hold the blade 350 in place by extending a full 360 degrees around the shank 126 of the driving shaft 118.

The overmolded portion in FIG. 11, like the overmolded portion in FIG. 10, contains openings 362 that match the raised protrusions in the collet assembly. With this over molded plastic arrangement, the blade 350 receives seven or in some embodiments, eight of the protrusions 172. The collet assembly holds the blade 350 in place, yet the pliable and deformable overmold permits easy blade removable. Further, the increased contact provided by the additional material helps further frictionally secure the blade in place and may provide surgeons with more control for precise cuts.

Figure 12:
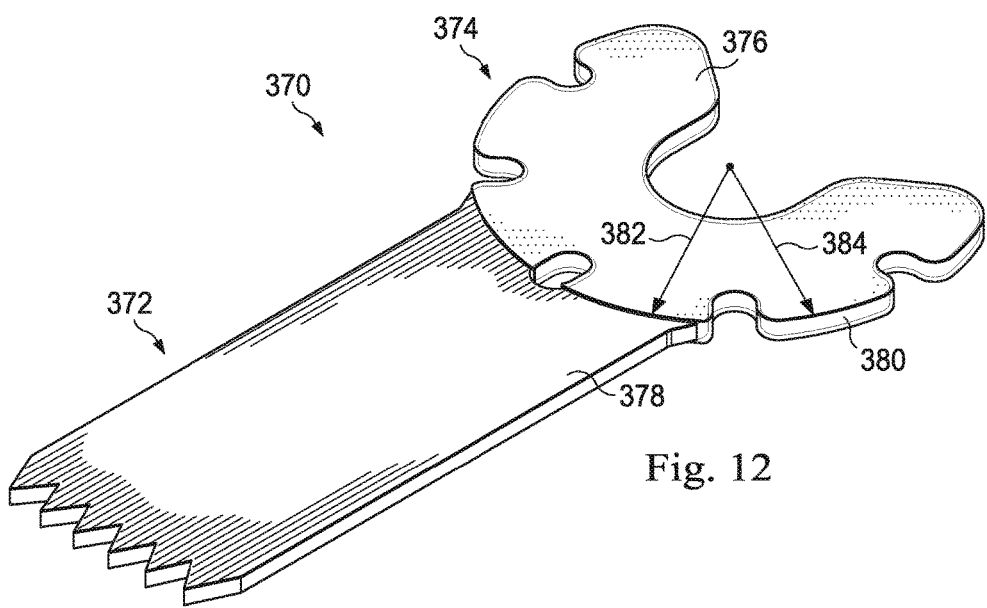

FIG. 12 shows an additional embodiment of an exemplary saw blade, referenced herein by the numeral 370. Here, the saw blade 370, like the saw blade 300 discussed above, includes a distal cutting end 372, a proximal end 374, and a bulbous head section 376. For reference, FIG. 12 identifies a shank 378 and an outer perimeter 380 of the bulbous head 376. The second material is overmolded about the first material to also form a part of the bulbous head 376. Here, the second material is formed on the blade 370 to cover primarily just the bulbous head section 376. Because of this, the second material does not extend down the shank 378 toward the distal end 372, but has a radius 382 that substantially matches the radius 384 of the outer perimeter 380 of the bulbous head 376. Accordingly, when placed in the collet assembly 116, the second material is substantially contained between the two blade contacting surfaces, with only the shank extending outwardly from the collet assembly 116.

The overmold in FIGS. 10-12 may be formed of a material softer than the sleeve 120 and driving shaft 118 materials. Accordingly, the overmold may reduce friction wear on the sleeve 120 and driving shaft 118 by yielding before the harder materials wear. Because the sleeve 120 and driving shaft 118 of the collet assembly 116 may be more expensive to manufacture than the saw blades, preserving the collet assembly may be beneficial to customers and may prolong the useful life of the associated surgical saw.

In one embodiment, the overmold is colored to provide information to a surgeon regarding, for example, a blade size, tooth type, or blade thickness. For example, a saw blade having a thickness of 0.010 inch includes a blue overmold and a blade having a thickness of 0.15 includes a red overmold. Accordingly, in some instances, a surgeon may select a desired blade from a blade set of a plurality of blades, with each blade having a colored overmold corresponding to a specific thickness, size, or tooth type.

Figure 13:
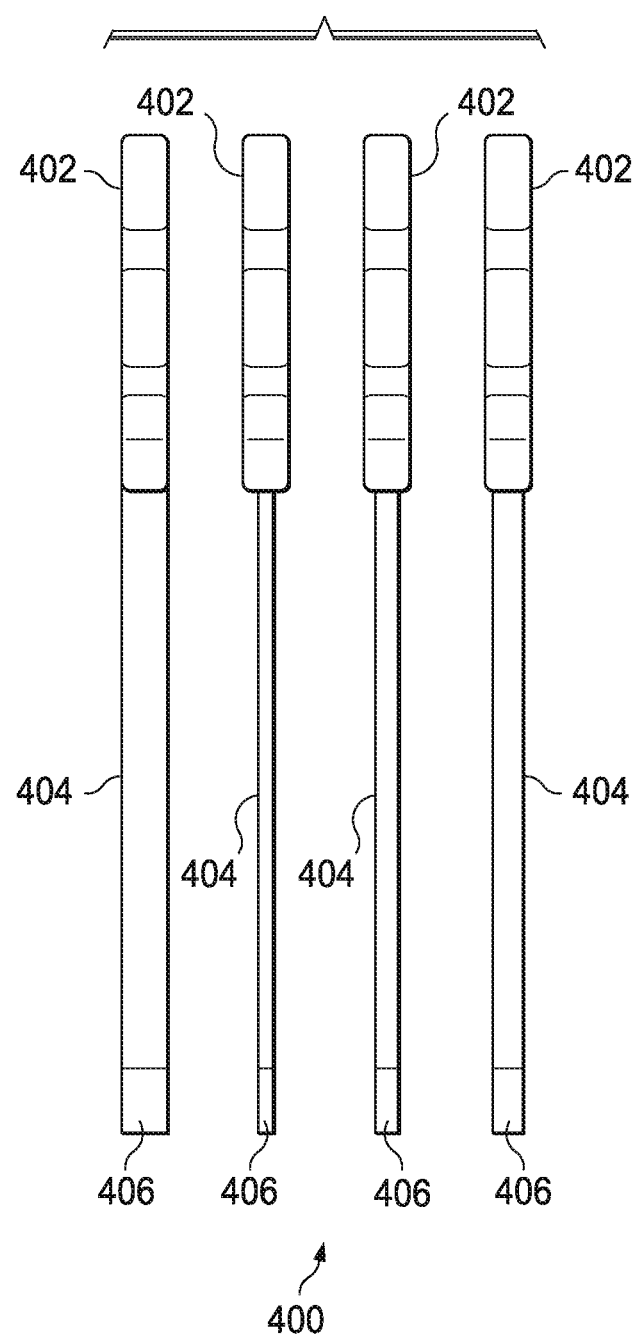
FIG. 13 is an illustration of an exemplary blade set having a plurality of micro-saw blades

FIG. 13 shows a side view of an exemplary blade set 400 usable with the collet assembly 116 disclosed herein. Each blade of the blade set 400 includes a proximal end 402 formed of a bulbous head, a shank 404, and distal cutting end 406. In this embodiment, however, the proximal end 402 of each blade of the blade set 400 has the same thickness, but the thicknesses of the shanks 404 and cutting edges 406 varies. Because the proximal end 402 has the same thickness, the head of each of the blades of the set fits within the receiving groove 146 on the shank 126 of the driving shaft 118 with the same amount of clearance or play for consistency and repeatability. Yet the blade shank 404 and distal cutting edge 406 vary so that a surgeon may select a blade with the desired thickness for the particular surgical application. For example, some blade sets may include blades that vary in thickness between 0.007 and 0.027 inch. The thickness of the proximal end 402 may be a result of an overmold as described above with respect to FIGS. 10 and 11, or alternatively, may be laminated or integrally formed of a single monolithic material. In this blade set 400, colored overmolding may identify the thickness of each cutting blade to permit a surgeon to distinguish one blade from another.

Figure 14:
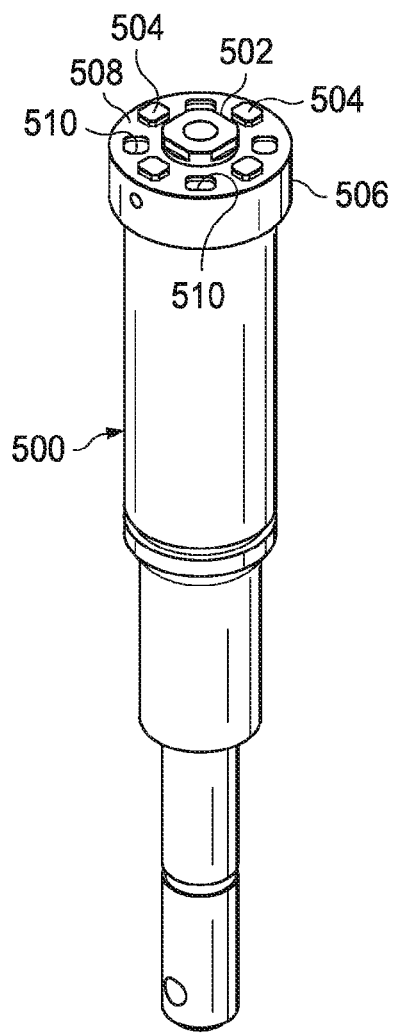
FIGS. 14 and 15 are illustrations of components of an alternative collet assembly.
Figure 15:
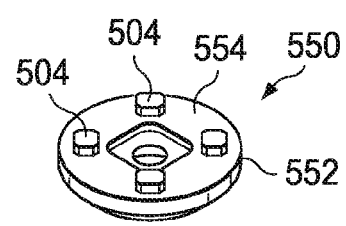

FIGS. 13 and 14 show components of an alternative collet assembly, with FIG. 14 showing an alternative sleeve 500 disposed about a shank 502 of a driving shaft, and with FIG. 15 showing a driving shaft head 550 separate from the shank 502. Protrusions 504 on the sleeve 500 and head 550 are spaced toward the respective perimeter edges 506, 552, in the manner discussed above. Accordingly, the description above regarding protrusion placement and placement of the receiving groove is equally applicable to the embodiment in FIGS. 13 and 14.

The sleeve in FIG. 14 includes a distally facing blade contacting surface 508 having both protrusions 504 and recessed receiving openings 510 spaced toward the perimeter edge 506 in the manner discussed above. In this embodiment, the protrusions 504 are rectangular or square rather than the cylindrical pins discussed above. It is contemplated that the driving shaft head 550 and the sleeve 500 would be used to secure a saw blade having corresponding shaped openings. In some embodiments, the protrusions or receiving openings are on the driving shaft, while in other embodiments, the sleeve includes some protrusions and the driving shaft includes other protrusions.

In FIG. 15, the head 550 is removable from the shank of the driving shaft, but may be attached using a fastener, such as a screw. The head 550 includes a proximally facing blade contacting surface 554 that includes protrusions 504 for engaging corresponding openings in a matching saw blade. In this embodiment, as described above, the protrusions 504 are spaced toward the outer perimeter edge.

Figure 16:
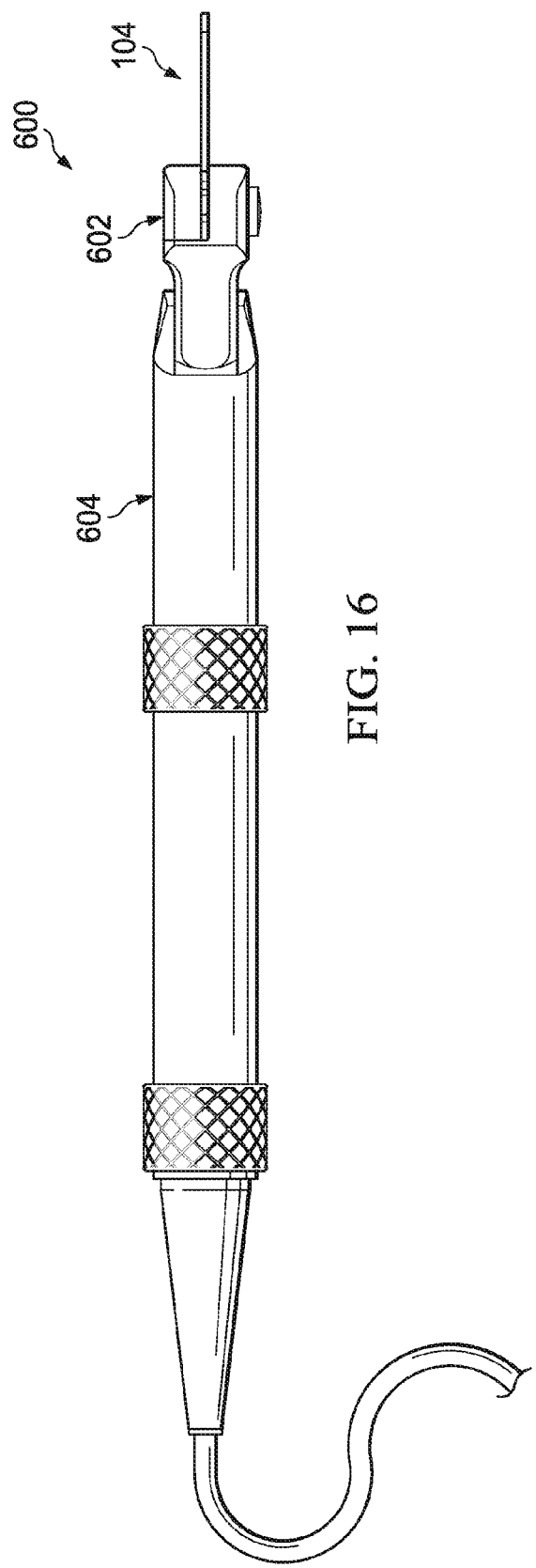
FIG. 16 is an illustration of an exemplary sagittal bone-cutting surgical system.

FIG. 16 shows a sagittal saw 600 for driving the saw blade 104. In this embodiment, the collet assembly 602 is arranged to secure the blade 104 in an axial direction relative to a saw handle 604. Accordingly, instead of having proximally and distally facing blade contacting surfaces, the collet assembly includes side-by-side blade contacting surfaces. However, like the oscillating saw 102 disclosed in FIGS. 1-6, the sagittal saw 600 includes protrusions disposed adjacent an exterior edge of the collet fixture, and the blade 104 is sized so that the outer perimeter of the head of the saw blade substantially corresponds to the edge of the collet assembly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgical cutting blade for use in cutting bone, the cutting blade comprising:
   a distal end portion having a plurality of cutting teeth;
   a shank portion extending from the distal end portion along a longitudinal axis; and
   a proximal end portion extending from the shank portion, the proximal end portion defined by a bulbous head having,
      a partially circular outer perimeter positioned about a center point defined by the bulbous head,
      a slot extending inwardly along the longitudinal axis and formed by a funnel shaped opening defined by two opposed edges radially extending toward the center point to a semi-circular slot edge concentric with the outer perimeter, and
      a plurality of openings formed into the outer perimeter.

2. The surgical cutting blade of claim 1, wherein the two opposed edges define an angle of about 90° to about 120°.

3. The surgical cutting blade of claim 1, wherein the two opposed edges are each substantially straight with rounded edges at each end to provide a smooth transition to the outer perimeter and the semi-circular slot edge.

4. The surgical cutting blade of claim 1, wherein each opening of the plurality of openings formed into the outer perimeter is shaped to be slot-like, having a semi-circular inner end and substantially parallel sides with rounded edges to provide a smooth transition from each opening to the outer perimeter.

5. The surgical cutting blade of claim 4, further comprising a centrally disposed opening that is positioned along the longitudinal axis defined by a closed slot.

6. The surgical cutting blade of claim 4, wherein the semi-circular inner end of each of the plurality of openings are spaced from the semi-circular slot edge more than half the distance between the outer perimeter and the semi-circular slot edge.

7. The surgical cutting blade of claim 1, wherein a concentric midline splits a distance between the partially circular outer perimeter and the semi-circular slot edge, wherein each opening of the plurality of openings is disposed offset from the midline.

8. The surgical cutting blade of claim 7, wherein innermost edge portions of each of the plurality of openings are disposed closer to the partially circular outer perimeter than to the semi-circular slot edge and spaced apart from the midline.

9. The surgical cutting blade of claim 1, wherein the cutting blade is formed of a first material and an overmold of a second material is positioned about the proximal end portion of the cutting blade to provide dampening and cushioning to the cutting blade.

10. The surgical cutting blade of claim 9, wherein the overmold is configured to have substantially the same profile as the proximal end portion of the cutting blade.

11. The surgical cutting blade of claim 9, wherein the overmold includes indicia to provide information to a user regarding the cutting blade.

12. The surgical cutting blade of claim 11, wherein the cutting blade and the overmold comprise a first cutting blade having a first overmold and a second cutting blade having a second overmold with the indicia being a first color associated with the first overmold and a second color associated with the second overmold, where the first color is different from the second color.

13. The surgical cutting blade of claim 12, wherein the first blade has a first blade thickness and the first overmold has a first overmold thickness and the second blade has a second blade thickness and the second overmold has a second overmold thickness, where the first blade thickness is different from the second blade thickness and the first overmold thickness is the same as the second overmold thickness.

14. A surgical cutting blade for use in cutting bone, the cutting blade comprising:
   a distal end portion having a plurality of cutting teeth;
   a shank portion extending from the distal end portion along a longitudinal axis; and
   a proximal end portion extending from the shank portion, the proximal end portion defined by a bulbous head having,
      a slot extending inwardly along the longitudinal axis having a slot edge formed about a center point defined by the bulbous head,
      an outer perimeter concentric with the center point, where a concentric midline splits a distance between the outer perimeter and the slot edge, and
      a plurality of openings formed in the outer perimeter, wherein the plurality of openings are disposed offset from the midline such that innermost edge portions of each opening are disposed closer to the outer perimeter than to the slot edge and spaced apart from the midline.

15. The surgical cutting blade of claim 14, wherein the outer perimeter is a partially circular outer perimeter and the slot edge is a semi-circular slot edge.

16. The surgical cutting blade of claim 14, wherein each opening of the plurality of openings formed into the outer perimeter is shaped to be slot-like, having a semi-circular inner end and substantially parallel sides with rounded edges to provide a smooth transition from each opening to the outer perimeter.

17. The surgical cutting blade of claim 14, wherein the cutting blade is formed of a first material and an overmold of a second material is positioned about the proximal end portion of the cutting blade to provide dampening and cushioning to the cutting blade.

18. A surgical cutting blade for use in cutting bone, the cutting blade comprising:
   a distal end portion having a plurality of cutting teeth;
   a shank portion extending from the distal end portion along a longitudinal axis;
   a proximal end portion extending from the shank portion, the proximal end portion defined by a bulbous head having,
      an outer perimeter concentric with a center point defined by the bulbous head,
      an inner perimeter concentric with the outer perimeter, and
      a plurality of slots formed into the outer perimeter and extending radially from the outer perimeter toward the center point; and
   an overmold formed over the proximal end portion.

19. The surgical cutting blade of claim 18, wherein the outer perimeter is a partially circular outer perimeter and the inner perimeter is a semi-circular perimeter.

20. The surgical cutting blade of claim 18, wherein innermost edge portions of each slot are disposed closer to the outer perimeter than the inner perimeter.

* * * * *